United States Patent [19]
Jenson

[11] Patent Number: 5,958,420
[45] Date of Patent: Sep. 28, 1999

[54] TREATMENT OF BURNS, CUTS, AND ABRASIONS OF THE SKIN

[75] Inventor: Marc S. Jenson, Salt Lake City, Utah

[73] Assignee: Nortrade Medical, Inc., Sandy, Utah

[21] Appl. No.: 09/041,923

[22] Filed: Mar. 13, 1998

Related U.S. Application Data

[60] Provisional application No. 60/040,756, Mar. 13, 1997.

[51] Int. Cl.$^6$ .................................................. A61K 35/78
[52] U.S. Cl. ............................................. 424/195.1
[58] Field of Search ........................................... 424/195.1

[56] References Cited

U.S. PATENT DOCUMENTS 5,009,890  4/1991  DiPippo .............................. 424/195.1

FOREIGN PATENT DOCUMENTS

| 559001 B2 | 2/1987 | Australia . |
| WO 92-GB1951 | 10/1992 | United Kingdom . |

OTHER PUBLICATIONS

Bassett et al. . Medical Journal of Australia 153(8) 455–8 (Abstract), 1990.

Suciu et al. Farmacia, 31(2), 93–100 Bucharest, Rom. (Abstract), 1983.

*Primary Examiner*—Raymond Henley, III
*Attorney, Agent, or Firm*—Clayton, Howarth & Cannon, P.C.

[57] ABSTRACT

A burn wound treatment system comprising a water-tight, sealed envelop containing a sterile, flexible, non-adherent dressing material and a sterile, stable, water soluble thixotropic gel. The gel of the present invention comprises tea tree oil and has the surprising capability of significantly lowering of the intradermal temperature of a burn wound upon topical application. The gel also inhibits infection and promotes healing of burn, chronic and acute wounds. The present invention preferably further comprises a waterproof barrier to be positioned and secured over the sterile dressing to protect against contamination and to prevent moisture loss.

6 Claims, 3 Drawing Sheets

TREATMENT OF BURNS, CUTS, AND ABRASIONS OF THE SKIN

This application claims the benefit of U.S. Provisional Application No. 60/040,756, filed Mar. 13, 1997.

BACKGROUND OF THE INVENTION

This invention relates to methods and apparatus permitting the prevention of and arresting of the progress of burn injuries, and creating an environment conducive to wound healing for acute and chronic wounds.

Burn injuries may be caused by exposure to heat, chemicals, electricity, or radiation, including solar radiation. Burn injuries are classified by the depth of penetration into the skin and underlying structures as well as the extent and location of the injury. The presence or absence of pain is not a good indicator of burn severity since very severe burns may be relatively pain-free due to extensive damage to the nerve endings.

When burn injuries occur, emergency treatment can help alleviate pain and can reduce the severity of after-effects of burn damage. Recommended emergency treatment methods often include the twin goals of preventing infection and cooling the burn site.

Since the skin is the first tissue to receive damage from burns, the loss of skin function creates most of the after-effects of burn damage. For example, intact, functioning skin provides a fluid barrier to prevent loss of body fluids. Large burn wounds can result in dehydration from fluid loss due to non-functioning, or nonexistent skin. Maintenance of moistness of the wound area is thus often desirable to prevent dehydration. Additionally, when a burn wound area is allowed to dry, movement of the area and surrounding skin is often very painful. When burn wounds are more localized, movement of the burn site is common. This is particularly true where the burn injury extends over an area where the skin is stretched as a joint is moved. Treatment methods currently employed do not often account for the flexure of a joint. Instead they may rely on immobilization of an entire patient, such as the treatment method disclosed in U.S. Pat. No. 3,986,505 issued to Power. The treatment method disclosed in Power teaches wrapping the patient within a sterile sheet and then enclosing the patient in a waterproof covering for transport. For smaller burn wounds, this method of treatment may be impractical.

To maintain moisture around a smaller wound, a local covering may be used. Typical materials used for covering, however, are generally made from a fabric or woven type material. These materials will not stretch, and hence limit movement of a burn site and apply unnecessary pressure on a burn site.

Of greatest threat, however, are the sometimes life threatening, complication of burn wounds due to infection. One of the primary functions of skin is to prevent contaminants from entering the body. When this protective barrier is lost due to burn injury, contaminants from multiple sources are free to enter the body and cause infection.

One goal of any emergency treatment method should thus be to prevent or reduce infection. This goal is usually achieved through limiting the contaminants entering the burn wound. Contamination may occur from clothing or debris that becomes embedded within the burned tissue. While this type of contamination may be washed away through emergency treatment methods under certain circumstances, removal and treatment for this type of contamination must usually wait until a patient can receive medical treatment at an appropriate facility.

Contamination may also occur while the burn wound is exposed to a non-sterile environment or from application of non-sterile coverings. While covering the burn wound is usually desirable, material that is applied to the burn wound may become saturated with leaking fluid. Subsequently, the material may adhere to the wound such that removal is very painful and possibly causes additional tissue damage. Moreover, depending on the nature of the material, shreds or fibers from the material may remain adhered to the wound and necessitate more extensive painful debridement. In addition, ever present airborne bacteria may enter the wounds of a burn patient while the tissue is unprotected by skin or dressings. It would therefore be advantageous to provide burn dressings that help keep bacteria from infecting a burn site while not adhering to the wound.

Heat generated at a burn site continues to damage the tissue even after removal from the direct burn injury source. Cooling the burn site helps to arrest the damage and can reduce the overall severity of the damage from a burn injury. Accordingly, a recommended immediate treatment of a burn wound is the gentle and continuous application of cool water. Application of cool water generally results in lessening of the pain and may cool the tissue enough to lessen the progression of the damage. Water, however, quickly flows away from the burn site and must be constantly replenished. Additionally, ice or ice water should not be used because of the risk of critical loss of body heat, and further potential tissue damage.

If continuous application is not possible, then repeated application of wet compresses is often suggested. These compresses must be kept cool with more water, however, as they will quickly absorb heat from the tissue. To provide as much cooling to the burn site as possible, the material used for the compresses should be capable of conforming to the shape of the burn site. Unfortunately, the fabric and woven material typically available for use in wet compresses do not conform well to areas that can be flexed or bent, such as joints of the limbs. Furthermore, the more complete the contact with the wet compresses, the greater the risk that the compresses will become saturated with leaking body fluid and stick to the burn wound.

Depending on the circumstances, clean cool water may not be immediately accessible or the patient's condition or location may make continuous application to the burn wound difficult or impossible. A method of transporting a burned patient in a sterile, moist environment such that the patient is kept cool and clean is disclosed in U.S. Pat. No. 3,986,505 issued to Power. Power teaches the use of a foam material saturated with an aqueous solution disposed within a flexible waterproof covering. The burned patient is essentially wrapped in a sterile sheet saturated with aqueous solution, positioned upon the foam material, and then enclosed within the flexible waterproof covering prior to transport. As previously mentioned, however, where the burn is relatively localized, this method of treatment may be impractical.

Another problem associated with burn victims is extinguishing burning clothing that may become ignited by exposure to a heat source. U.S. Pat. No. 3,902,559 issued to Everinghingham et al., herein incorporated by reference, discloses a means of extinguishing burning clothing on humans comprising application of a fabric carrier saturated with an aqueous solution of a thickening agent.

The above-described approach permits extinction of a fire source and swathing of the patient in a moist environment. The covering provides protection from environmental contamination and the moistness promotes some cooling effect. However, neither of the above-described approaches effects significant lowering of the intradermal temperature at the burn wound site.

It would, therefore, be advantageous to provide methods and apparatus for improved treatment of a burn wound that permit significant lowering of the intradermal temperature within the burn wound and maintenance of a lowered intradermal temperature within the burn wound such that the extent of the burn wound may be limited and the patient be more comfortable. It would additionally be advantageous to provide means for substantially reducing the intradermal temperature through the application of a burn wound treatment composition that also inhibits infection, promotes healing of the tissue, and is easily removed with water so that removal does not cause the patient additional pain or tissue damage. Moreover, it would be advantageous to provide this capability with a flexible material that conforms to the burn site and stretches when the site is moved so that no unnecessary pressure is exerted on the burn site.

A potential side effect of reducing of the intradermal temperature is hypothermia. Therefore, it would also be advantageous to provide a system that is effective at reducing intradermal temperature without the threat of overcooling, heat loss, and ensuing hypothermia.

Acute and chronic wounds include pressure ulcers (decubitus or bed sores), venous and arterial ulcers, and diabetic ulcers. Pressure ulcers are the most common form of skin damage and occur when externally applied pressure exceeds capillary closing pressure. With the unrelieved pressure, tissue damage occurs, creating a wound. This type of wound is most common in people whose general health has been compromised and usually occurs over a bony prominence. Pressure ulcers are often found in patients who are confined to bed or wheelchairs. It is estimated that the treatment of pressure ulcers costs the U.S. healthcare system over 8.5 billion dollars annually. Venous and arterial ulcers generally occur on the legs or feet and are the result of some type of vascular damage. These wounds occur most frequently when a combination of poor blood flow and high blood pressure exist. Diabetic ulcers are sores that occur on the foot of a patient with diabetes. They have many contributing factors including trauma, poor circulation, and an abnormality of the nervous system. Current treatment protocols involve the use of products that provide a moist wound environment.

In 1961, George Winter first experimented with the promotion of a moist wound environment in the treatment of injury. His experiments showed that by keeping the wound surface damp, healing was accelerated. This result was first published in medical journals in 1971. The first hydrogel was not commercially introduced until 1985. Many now consider a moist environment preferable in the treatment of wounds. Research data suggest that the body's natural healing processes of autolytic debridement, epithelialization, granulation, and maturation are enhanced in a moist environment. Healing can occur more quickly in a moist healing environment than in wounds left exposed to air. However, the threat of infection remains an ongoing concern, and, typically, products that are bacteriostatic unfortunately are also cytotoxic. In other words, they inhibit or stop the growth of new skin cells, thus slowing the wound-healing process.

Many health care providers do not use a moist protocol for infected wounds because a moist environment has been shown to be conducive to growth of bacteria. It would, therefore be advantageous to provide methods and apparatus for improved moist treatment of an infected acute or chronic wound that would inhibit the growth of bacteria, while not inhibiting the growth of new cells. In addition, odor control in chronic wounds has become an important concern of health care workers and caregivers. An added advantage in this apparatus would be to help maintain an odor free wound site.

In view of the foregoing, it will be appreciated that providing methods and apparatus for treating wounds with a moist environment while inhibiting microbial infection and odors would be a significant advancement in the art.

BRIEF SUMMARY OF THE INVENTION

It is an object of the present invention to provide apparatus and methods permitting improved treatment of burn wounds by application of a burn wound treatment composition capable of quickly effecting a substantial lowering of the intradermal temperature of the burn wound to arrest progression of heat damage within the tissue.

It is another object of the present invention to provide apparatus and methods permitting improved treatment of burn wounds by application of a burn wound treatment composition capable of maintaining a lowered intradermal temperature of the burn wound to contribute to the patient's comfort for a time period until further medical attention can be obtained.

It is yet a further object of the present invention to provide apparatus and methods permitting improved treatment of burn, acute, and chronic wounds by covering the wound with a sterile, non-adherent, flexible, expandable, non-fibrous and non-woven dressing for smaller wounds, and a specially woven wool dressing for larger wounds, saturated with the wound treatment composition, which maintains contact between the wound and the wound treatment composition and protects the wound from environmental contamination yet permits movement of the injured area, if necessary or desired, and avoids problems associated with adherence of the dressing or portions of the dressing to the wound.

Yet another object of the present invention is to provide apparatus and methods permitting improved treatment of burn, acute, and chronic wounds by covering the dressing with a protective moisture barrier to maintain the sterility and moistness of the dressing and prevent hypothermia.

A still further object of the present invention is to provide an apparatus capable of preventing burn injuries by placing the apparatus on the individual prior to exposure to heat or other burn generating environments. It is also an object of the present invention to provide apparatus and methods permitting improved treatment of burn, acute, and chronic wounds by application of a wound treatment composition that also inhibits infection, promotes healing of the tissue, and is easily removed with water so that removal does not cause the patient additional pain or tissue damage.

To achieve the foregoing objects, and in accordance with the invention as embodied and broadly described herein, the wound treatment composition of the present invention effects significant lowering of intradermal temperature of a burn wound. The wound treatment composition of the present invention also inhibits infection and promotes healing of a wound. In addition, a sterile dressing material used with the present invention is capable of retaining ample amounts of the wound treatment composition to permit suffusion of the wound for a period of time. The dressing, material will not adhere to the wound surface and will not disintegrate so that the dressing may be easily and completely removed when desired. If the dressing material is allowed to remain on the wound for an extended period of time, that is, a period of time longer than recommended, the dressing may begin to adhere to the wound. The dressing can, however, be loosened and removed by saturating the dressing with sterile water before removing the dressing. The present invention preferably further comprises a waterproof barrier to be positioned and secured over the sterile dressing to protect against contamination and to prevent moisture loss and hypothermia.

The burn wound treatment composition of the present invention comprises several ingredients including tea tree oil to form a thixotropic gel formulation. The biodegradable gel is non-toxic, non-irritating, and non-staining, and is stable over a wide temperature range. The moist gel inhibits bonding of dressings to the wound and permits easy removal for wound inspection and treatment. The gel is primarily water so it can be easily removed by water flushing if desired. Unlike water, however, the gel formulation will not readily flow away from the wound. A significant property of the composition is the ability to significantly and continuously cool a surface. The cooling is greater than the cooling provided by evaporation or radiation or the combination of these two heat transfer methods. The gel conducts large amounts of heat away from the site. Surprisingly, during testing, it has been discovered that this heat removal and overall lessening of the temperature of a site can even occur when significant additional heat is being added.

There are numerous possible applications for the heat absorbing and dissipating properties of the wound treatment composition. For example, the composition could provide a reassuring method of shielding dangerous combustible material in the proximity of a fire. For example, a large sheet saturated with the gel may be wrapped around propane tanks to reduce the temperature therein and reduce the risk of explosion.

The ability to withdraw destructive heat from burn wounds provides a highly effective trauma treatment that avoids the extreme shock effects which may ensue from ice treatment.

Preferred embodiment of the present invention include a tri-laminate package consisting of polyethylene, polyester, and aluminized foil package or similar material. Included inside the dressing package is a soft, pliable, foam material saturated with the wound treatment composition. The blanket packaging includes a specially woven wool material saturated with the wound treatment composition. In use, this blanket embodiment can be placed on a burn victim upon discovering the victim in a burning building.

DETAILED DESCRIPTION

Figure 1:
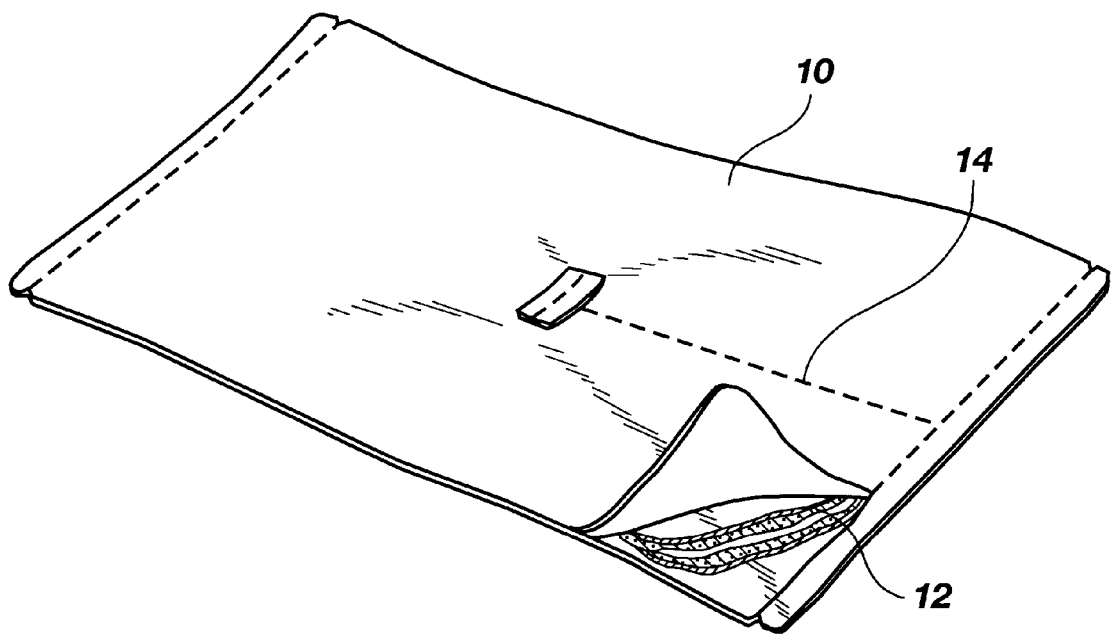
FIG. 1 shows a perspective view of an illustrative embodiment of the invention showing the packaging material of the present invention with a cutaway revealing the sterile dressing within the packaging material.

Before the present methods for treatment of wounds are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a composition containing "a surfactant" includes a mixture of two or more of such surfactants, reference to "a preservative" includes reference to one or more of such preservatives, and reference to "a thickener" includes reference to a mixture of two or more thickeners.

In describing and claiming the present invention, the following terminology will be used in accordance with the definitions set out below.

As used herein, "tea tree oil," "melaleuca oil," and "oil of melaleuca" refer to distillates of the leaves of the Australian tree, *Melaleuca alternifolia*. Tea tree oil is assigned Chemical Abstract number 68647-73-4 and is commercially available from a variety of sources. Tea tree oil is recognized as having properties as a solvent, antiseptic, antibacterial, antifungal, and pain reliever, as well as other uses. Melaleuca oil has been used in soaps, shampoos, hand creams, toothpastes, and household cleaners, as well as for treatment of warts and oral candidiasis.

As used herein, "effective amount" means an amount of tea tree oil sufficient to yield a selected therapeutic response without undue adverse effects (such as toxicity, irritation, or allergic response) commensurate with a reasonable benefit/risk ratio when used in the manner of this invention. As used in the present application, an effective amount will preferably be in the range of about 0.01–20% by weight and more preferably about 0.1–10% by weight.

As used herein, "biocompatible" means safe for use on skin of a warm-blooded animal without undue adverse effects (such as toxicity, irritation, or allergic response) commensurate with a reasonable benefit/risk ratio when used in the manner of this invention.

As used herein, "warm-blooded animal" includes humans as well as non-humans.

As used herein, "hydrogel" means a hydrophilic gel comprising a gel matrix and water. Examples of matrix materials suitable for use in the present invention include: carboxymethylcellulose (such as the CARBOPOL series of materials from Union Carbide), hydroxypropylcellulose, hydroxyethylcellulose, hydroxymethylcellulose, methylcellulose, polyvinylpyrrolidone, polyvinyl alcohol, and mixtures thereof and the like. Such matrix materials will generally be present in amounts ranging from about 0.1–10% by weight.

The composition according to the present invention comprises a stable, water-soluble, biocompatible, thixotropic hydrogel and an effective amount of tea tree oil, wherein the tea tree oil is intimately admixed with the hydrogel. The composition can further comprise one or more members selected from the group consisting of preservatives, surfactants, solvents, thickeners, pH adjusting agents, bonding agents, and mixtures thereof, and the like.

For example, in a preferred embodiment, the composition comprises about 0.0003–0.5% by weight of a preservative. Preferred preservatives can be selected from the group consisting of chlorobutanol, triclosan, methylparaben, propylparaben, methylchloroisothiazolinone, methylisothiazolinone, and diazolidinyl urea.

In another preferred embodiment, the composition comprises about 0.01–16% by weight of a surfactant. Preferred surfactants are selected from the group consisting of polyoxyethylene alkylphenols, polyoxyethylene alcohols, alkyl ether sulfates, and alkyl sulfates.

The pH of the composition is preferably maintained in the range of about pH 5.5–7.0. Acids, bases, and buffers can be according to methods well known in the art for adjusting the pH of the composition.

Solvents suitable for use in the present composition, in addition to the water that makes up the hydrogel, include lower alcohols and glycols, as are well known in the art. Such solvents may be advantageous for solubilizing certain optional ingredients of the composition, such as a preservative.

Wounds to the skin that can be treated according to the present invention include burn wounds, sunburn, cuts, abrasions, and acute and chronic wounds and the like.

Treatment of burn, acute, and chronic wounds typically is directed to keeping the wound as clean as possible and making the patient as comfortable as possible. It has been recognized that keeping the wound moist is advantageous to patient comfort. While maintaining a moist environment will effect some cooling of the tissue, it would be advantageous to be able to effect significant lowering of the intradermal temperature of the burn wound, which helps to arrest further damage which may occur due to heat within the tissues.

Accordingly, it would be advantageous to provide a method and apparatus for improved treatment of a burn wound that permits significant lowering of the intradermal temperature of the burn wound such that the extent of the burn wound may be limited.

In addition, maintenance of a lowered intradermal temperature of the burn wound will contribute to patient comfort until further medical treatment can be obtained. It would be additionally advantageous to provide a topical burn wound treatment composition capable of substantially reducing the intradermal temperature of a burn wound which also inhibits infection, promotes healing, of the tissue, and is easily removed with water so that removal does not cause the patient additional pain or tissue damage.

Moreover, it would be advantageous to provide a method and apparatus for protecting the burn wound from environmental contamination during administration of the topical burn wound treatment composition. Accordingly, the present invention provides apparatus and methods permitting improved treatment of burn wounds by covering the wound with a sterile, non-adherent, flexible, expandable, non-fibrous and non-woven dressing or specially woven wool blanket, saturated with the burn wound treatment composition to maintain contact between the burn wound and the burn wound treatment composition and also to protect the burn wound from environmental contamination yet permit movement of the injured area, if necessary or desired, and avoid problems associated with adherence of the dressing or portions of the dressing to the burn wound.

In addition, the present invention includes a protective moisture barrier to contribute to the sterility of the dressing and to maintain the moistness of the dressing. Sterility is enhanced by the bacteriostatic properties of the wound treatment composition, as well as the shielding action of the barrier's physical presence. An additional barrier to bacteria and contamination is the packaging utilized with the present invention.

It has been discovered that the wound treatment composition of the present invention effects significant lowering of the intradermal temperature of a burn wound. It has been further discovered that the wound treatment composition of the present invention inhibits infection and promotes healing of burn, acute, and chronic wounds. In addition, the sterile dressing material used with the present invention is capable of retaining ample amounts of the wound treatment composition to permit suffusion of the wound for a period of time. The dressing material will not adhere to the wound surface and will not disintegrate so that the dressing may be easily and completely removed from the wound when desired. The present invention preferably further comprises a waterproof barrier to be positioned and secured over the sterile dressing to protect against contamination and to prevent moisture loss. A preferred embodiment of the present invention is illustrated in FIG. 1. Disposed within the packaging material or envelope 10, shown in cutaway, is the flexible, sterile dressing 12 according to the present invention. As used within the scope of this patent, envelope should be construed to include all containers and packaging material of sufficient size to enclose the flexible, sterile dressing. The envelope can be of any shape or size. For example, it may be desirable to shape the envelope so as to fit a specific limb or body part such as a hand or foot. Additionally, the envelope may be designed primarily for convenience in storage or carrying. For larger versions of the sterile dressing, the envelope may be designed for easy removal and deployment (unfolding) of the sterile dressing.

The wound treatment composition of the present invention comprises tea tree oil and other ingredients in a thixotropic gel formulation. Tea tree oil, or *Melaleuca alternifolia*, is a natural plant extract. The unique wound treatment composition, in addition to creating a moist, soothing environment, is also inherently bacteriostatic. Other compositions and formulations which are bacteriostatic unfortunately are also cytotoxic. In other words, they inhibit or stop the growth of new skin cells, thus slowing the wound-healing process. Independent clinical testing has demonstrated that even though this unique wound treatment composition inhibits the growth of bacteria, it does not inhibit the growth of new cells. In fact, the composition encourages new skin cell growth. Testing has also shown that melaleuca oil dissolves pus and aids in the debridement (wound cleansing) process. It helps leave the surface of wounds clean and odor free. The odor of chronic wounds is a major concern of health care workers and caregivers. The effectiveness of Melaleuca is increased in the presence of blood and organic material, rather than decreased as is the case with other bacteriostatic products. Together, these two features represent a potential breakthrough in wound treatment by allowing healing to begin or continue while the wound is cleaned and kept free of infection. The emergence of methicillin- and mupirocin-resistant Staphlococcus aureus organisms (MRSA) is also creating a serious threat to the ability of hospital staffs to manage the spreading of common harmful pathogens. Extensive independent testing has proven that oil of *Melaleuca alternifolia* has broad spectrum antimicrobial activity and is non-toxic when topically applied. Of 60 MRSA organisms tested against melaleuca oil, all were susceptible to it. The use of cleansers, lotions, and other products containing this unique wound treatment composition will be significant in treatment of MRSA as well as a deterrent against the spread of infectious bacteria.

The biodegradable composition is non-toxic, non-irritating, and non-staining. It is stable over a wide temperature range from approximately 50° C. to 95° C. and has a pH in the 5.5 to 7.0 range. The moist gel inhibits bonding of dressings to the wound and permits easy removal for wound inspection and treatment. The gel is primarily water so it can be easily removed by water flushing if desired. Unlike water, however, the gel formulation will not readily flow away from the burn wound.

Recent research has shown that melaleuca oil has the following medical characteristics relevant to the instant invention. (1) Melaleuca oil is highly bacteriostatic; it helps to maintain a bacteria-free environment and prevents healthy tissue from being compromised or destroyed by infection. (2) Melaleuca oil exhibits low cytotoxicity; it causes no skin irritation or damage to surrounding healthy tissue when used as directed and does not destroy newly forming skin cells. (3) Melaleuca oil is water soluble; it dissolves pus and leaves the surface of a wound clean and deodorized. (4) Melaleuca oil is bio-activated; the effectiveness of melaleuca oil is increased in the presence of blood and organic material, rather than decreased. (5) Melaleuca oil penetrates unbroken skin and thus provides disinfecting action to subcutaneous layers Melaleuca oil is considered to be safe and effective on all kinds of cuts and abrasions, surgical wounds, diabetic and mouth ulcers and foot fungi.

It has been discovered, however, that the wound treatment composition of the present invention has in addition to the recognized beneficial properties of tea tree oil itself, by virtue of the combination of its constituent elements, the additional capability of significantly lowering the intradermal temperature of a burn wound. Although tea tree oil itself demonstrates some cooling, the combination of elements has an increased capability to lower intradermal temperature upon contact thus inhibiting burn progression. This capacity was demonstrated in a comparison test conducted in an independent laboratory. Conclusions drawn were that application of the topical gel resulted in a greater than four fold increase in the length of transition zone from complete necrosis to uninjured tissue as compared to similar cutaneous burns in mice treated with sterile saline for forty minutes after thermal injury, see Example 3. Observations included a high efficiency heat capacity available for immediate or rapid cooling of the burn wound and suspected anesthetic and antimicrobial effects.

In regard to the bactericidal and wound healing properties of the unique wound composition were illustrated in additional testing performed in an independent laboratory. Conducted on a porcine model, it compared the effects of long-term treatment of the wound treatment composition and the most commonly used drug (silver sulfadiazine) on thermal wounds/burn wounds. Wound healing was assessed by several different methods including measuring blood flow to the wounded area, visual examination and histological assessments, see Example 4. The unique wound composition hydrogel was more effective in the long-term treatment of thermal wounds than the drug silver sulfadiazine, and was shown to inhibit the growth of bacteria better than Povidone Iodine, BETADYNE, or pure melaleuca oil.

The wound treatment composition is unique in that it crosses over into several other wound dressing categories including hydrocolloid and foam. It is also bacteriostatic while being non-cytotoxic, which makes it unique among moist/synthetic wound dressings. These characteristics contribute to its potential for use in a wide range of clinical applications in both acute and chronic wound treatment.

A blanket impregnated with the burn wound treatment composition of the present invention could be applied as a lifesaver to stifle flames on a burning person while simultaneously providing initial beneficial treatment of burns the victim may have sustained. Application of the sterile blanket also provides protection from environmental contamination.

It is well known that wool has intrinsic insulating and fire resistant properties. Wool has traditionally been used to smother flames and protect from fire. Heat protection was markedly improved in a wool blanket impregnated with the burn wound treatment composition (test gel) of the present invention as compared to a dry wool blanket and a water-saturated wool blanket when the blankets were exposed to the flame from an oxy-acetylene torch. The torch flame temperature was 1150° C. and the torch was set at a fixed distance of 15 cm from each test blanket and the results of this test are presented in the following table:

| MATERIAL | BURN THROUGH TIME |
| --- | --- |
| Dry Wool Blanket | Instantaneous |
| Water saturated wool blanket | 12 seconds |
| Test gel-impregnated blanket | 1 minute 27 seconds |

As can be seen from the table, the test gel-impregnated blanket withstood the torch flame more than 8 times longer than the water-saturated blanket. This demonstrates very significant heat protection with the wound treatment composition of the present invention. It can be seen that application of a dressing saturated with the wound treatment composition of the present invention would provide superior cooling to application of water-soaked dressings.

To test the heat dissipation capabilities of the wound treatment composition of the present invention, a stem thermometer was subjected at a fixed point to a butane gas blow torch flame, having a flame temperature of approximately 1150° C., until the stem temperature reached 2500° C. The stem of the thermometer was then covered with a single 10 cm×10 cm layer of a blanket impregnated with the wound treatment composition of the present invention. The temperature of the stem was observed to immediately begin dropping. Remarkably, the temperature continued to drop even when the butane flame was reapplied to the covered stem.

In conclusion, the wound treatment composition of the present invention demonstrates an exceptional ability to absorb and dissipate heat.

There are numerous possible applications of the surprising heat absorbing and dissipating properties of the wound treatment composition. For example, the composition could provide a reassuring method of shielding dangerous combustible material in the proximity of a fire. The ability to withdraw destructive heat from burn wounds provides a highly effective trauma treatment which avoids the extreme shock effects which may ensue from ice treatment.

Returning to the preferred embodiment illustrated in FIG. 1, the flexible, sterile dressing is saturated with an excess quantity of the sterile wound treatment composition. The flexible dressing can be shaped to conform to the desired body surface and even pushed into crevices, such as between fingers and toes. In addition, the excess quantity of the wound treatment composition permits the composition to flow into any spaces not actually contacted by the dressing so that the entire wound surface can be covered with the wound treatment composition. The sterile dressing material is preferably an extra soft elastic, inert plastic foam sheet capable of being saturated with the wound treatment composition. The preferred foam dressing base is thick enough to efficiently cover a wound and is also elastic enough to accommodate possible swelling of the tissue or to permit flexing of joints in the area of the wound. Because the inert foam is non-woven and non-fibrous, there is little possibility that threads, strands, fibers, etc. will separate from the dressing material and become embedded within the burn wound.

In a preferred embodiment, the envelope, in addition to being waterproof, can be sealed closed in a fluid-tight manner. An example of suitable material would be a aluminum foil or aluminized mylar or other suitable material. The envelope and the enclosed sterile dressing can be of various sizes adaptable to various-sizes of wounds. For example, it has been found that a 20 cm×20 cm sized dressing is suitable for many applications including a burned hand or foot as described below. A 10 cm×10 cm dressing might be suitable for smaller burn wounds while a larger size dressing, such as a 60 cm×40 cm, would be appropriate for covering most limbs and torsos. Even the larger "blanket" size dressings would be appropriate for covering very large areas or to envelope a person entirely. At least one portion of the sealed envelope, for example, an end portion, is preferably adapted to be easily torn open to ensure rapid access to the saturated sterile dressing. Such tearable openings are shown by the dotted lines designated 14 in FIG. 1.

In addition to being easily torn open, the envelope may be cut open at any point so as to form an opening suitable for inserting a portion of a patient's body containing a burn wound.

In order to treat large scale burns, blanket sized dressings may also be provided. These dressings can be contained in an appropriately sized envelope which aids in removal and unfolding of the dressing for rapid deployment. These blanket-sized dressings can be used in conjunction with a moisture barrier, such as a mylar sheet, to enclose an entire patient, or a significant portion of a burn victim, while preventing moisture loss and hypothermia. This embodiment may be particularly useful where a burn victim must be removed from a burning area.

The cooling ability of the treatment system described herein is proportional to the amount of thixotropic gel formulation carried within the flexible, sterile dressing.

It will be appreciated that the present invention may be embodied in other specific forms without departing from its spirit or essential characteristics. The described embodiments are to be considered in all respects only as illustrative and not restrictive, and the scope of the invention is indicated by the appended claims rather than by the foregoing description or the following examples. All changes which come within the meaning and range of equivalency of the claims are to be embraced within their scope.

EXAMPLE 1

In this example, there is described the making of an illustrative topical wound treatment material according to the present invention. The material comprises the following ingredients in percentage by weight.

| Ingredient | Wt. % |
| --- | --- |
| Chlorobutanol | 0.1% |
| Ethanol | 0.025% |
| Polyethyleneoxide alkylphenol | 0.05% |
| Triclosan | 0.1% |
| Carboxymethylcellulose | 0.52% |
| Propylene glycol | 1.5% |
| Tea tree oil | 1.03% |
| Triethanolamine | 0.52% |
| Water | 96.155% |

The composition is prepared by dissolving the chlorobutanol in the ethanol. The polyoxyethylene alkylphenol is then added, followed by the triclosan and carboxymethylcellulose. This mixture is stirred thoroughly. Propylene glycol is then added and stirred thoroughly into the mixture. A portion of the water is then added and mixed thoroughly to result in a concentrated gel base. The remainder of the water is placed in a separate container and the concentrated gel based is added with agitation until the mixture is smooth. The tea tree oil is then added and mixed into the gel. Finally, the triethanolamine is added and mixed with the gel. Mixing is continued until a smooth white thixotropic gel is formed.

EXAMPLE 2

In this example, illustrative formulations according to the present invention are described. Amounts are expressed in percent by weight.

Formulation A

| Water | 78% |
| --- | --- |
| Carboxymethylcellulose | 2% |
| Tea tree oil | 20% |

Formulation B

| Water | 98.9% |
| --- | --- |
| Hydroxypropylcellulose | 1% |
| Tea tree oil | 0.1% |

Formulation C

| Water | 94.9% |
| --- | --- |
| Hydroxyethylcellulose | 1.5% |
| Methylparaben | 0.5% |
| Ethanol | 0.1% |
| Tea tree oil | 3.0% |

Formulation D

| Water | 97.7% |
| --- | --- |
| Hydroxymethylcellulose | 0.8% |
| Propylparaben | 0.25% |
| Methylparaben | 0.25% |
| Ethanol | 0.5% |
| Tea tree oil | 0.5% |

Formulation E

| Water | 98.5% |
|---|---|
| Methylcellulose | 0.6% |
| Propylene glycol | 0.1% |
| Ethanol | 0.1% |
| Chlorobutanol | 0.2% |
| Sodium lauryl sulfate | 0.1% |
| Triethanolamine | 0.4% |

EXAMPLE 3

The extent and depth of burn injury is not only determined by temperature and duration of the thermal insult, but also by the response to injury. Attempts to modulate this response take the form of adequate fluid resuscitation and optimal wound care. In the present example, the margins of full-thickness burn injuries were examined morphometrically after topical application of a composition according to the present invention in a murine model for evaluating the effect of immediate treatment of the burn wound with the present composition as compared to a saline control.

Figure 2:
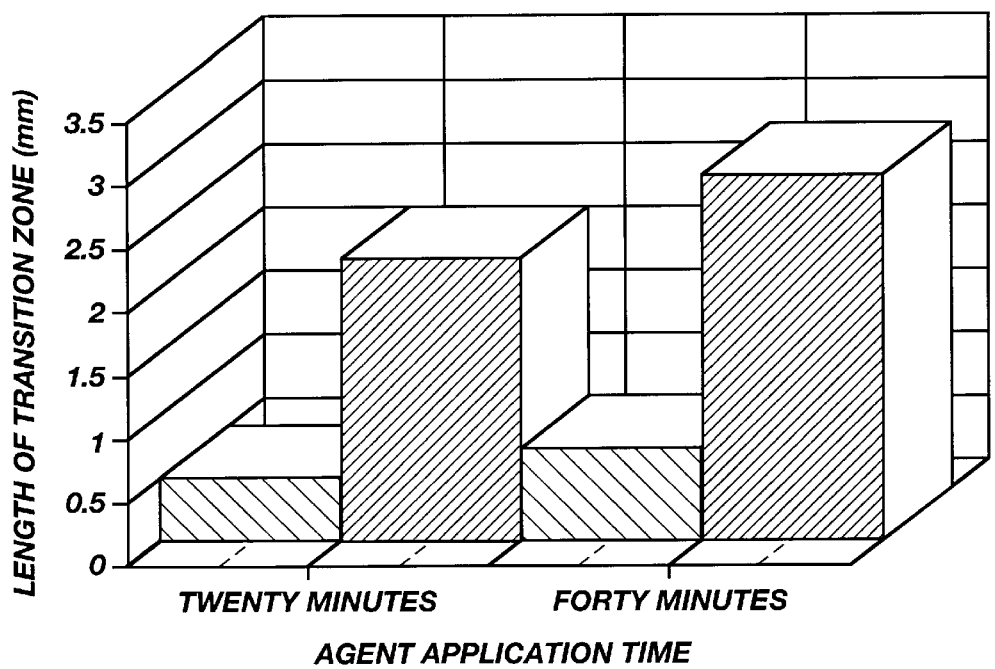
FIG. 2 shows a histogram of the length of transition zone as a function of time and treatment with either saline control (light bars) or the present composition (dark bars).

Twenty C3H mice were injured with 20% TBSA scald burn (70° C., 6 sec.). Burn wounds were immediately treated for 20 or 40 minutes with topical application of room-temperature saline or a composition prepared according to the procedure of Example 1. Mice were sacrificed on post-burn day 2 for examination of H&E sections of the burn wound. Micrometric measurements of the distance from full-thickness necrosis to normal skin was performed. Regions of total cutaneous necrosis were identified by the absence of viable surface and appendage epithelium. Regions of partial epithelial survival were identified by histological evidence of viable appendage or surface keratinocytes. Regions of normal cutaneous histology were also identified. These results are summarized in FIG. 2.

Murine cutaneous burns treated with the present composition for 40 minutes immediately after the thermal injury had larger transitional zones from complete necrosis to uninjured tissue as compared to similar cutaneous burns in mice treated with sterile saline for 40 minutes immediately after thermal injury. Application of the present topical gel resulted in greater than a four-fold increase in the length of the transition zone ($p<0.0002$; ANOVA, Scheffe F-test). The duration of application (20 or 40 minutes) was not a significant factor in the size of the transition zone. These results show that immediate topical the treatment of the full-thickness burn wound in mice results in a larger transition zone from complete necrosis to uninjured tissue using the present composition as compared to the saline control. These results suggest a salubrious effect on partial thickness thermal injuries.

EXAMPLE 4

Thermal injury results in tissue damage to the skin that includes damage to the microcirculation and increased capillary permeability leading to extravasation of fluid and blood cells, resulting in edema and shock. Superficial partial-thickness burns, involving only the epidermis and superficial dermis of the skin, are pink or red with thin-walled blisters. Deep partial-thickness burns can re-epithelialize and heal without grafting. However, deep partial-thickness injuries can develop hypertrophic scarring or progress to full thickness injuries if the microcirculation is completely obliterated. Burns that extend beyond the dermis into subcutaneous tissue are classified as third degree burns, which require grafting. A major component of third degree burns is dermal ischemic necrosis.

In this example, the effects of treating a deep second degree burn with either a composition according to the present invention or the most frequently used dressing (sulfadiazine) for wounds of this type were compared. Forty-kilogram pigs each received sixteen 25-$cm^2$ contact burns administered under inhalation anesthesia with 85° C. aluminum blocks applied to dorsal skin for 10 seconds. Wounds were dressed with either a composition prepared according to Example 1 or with sulfadiazine within thirty minutes of the burn injury. Dressings were changed daily for four days and then every other day until day ten post-injury. Cutaneous blood flow was measured by laser-doppler flowmetry prior to the burn, 30 min. thereafter, and at every dressing change. Wound biopsies were obtained on post-burn days 3 and 10 for histomorphometry to evalute epithelial (hematoxylin and eosin stains) and mesenchymal (vimentin) responses.

Figure 3:
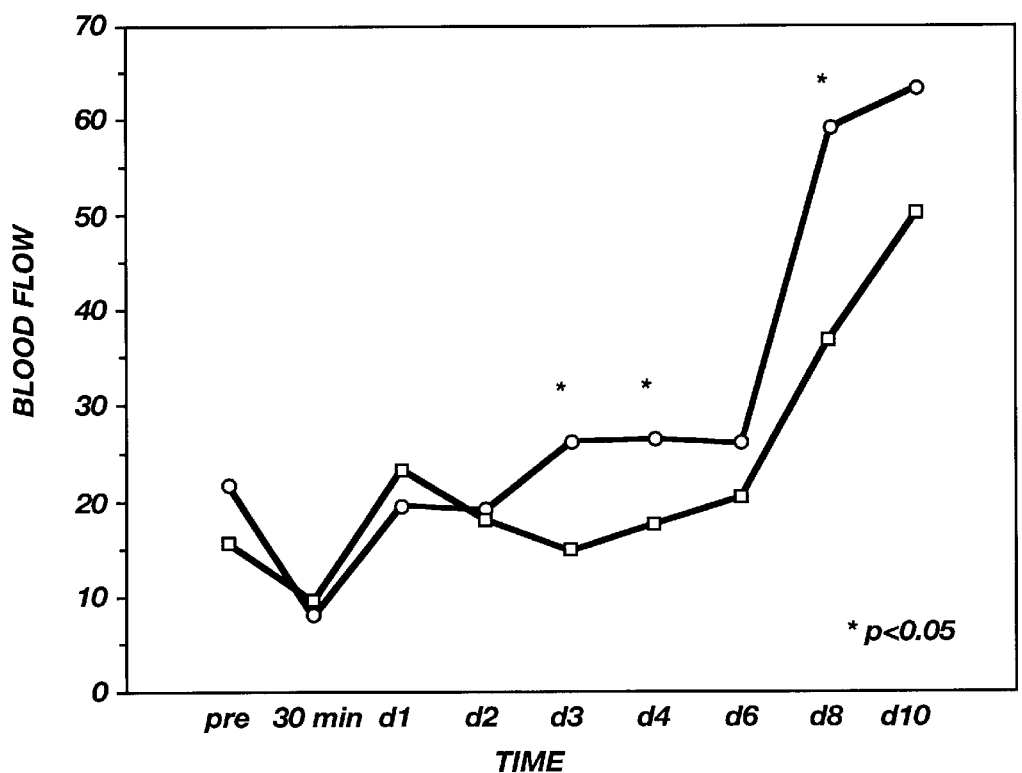
FIG. 3 shows a plot of blood flow as measured by laser-doppler flowmetry as a function of time for treatment with sulfadiazine (□) and the present composition (○).

The results of the blood flow measurements are shown in FIG. 3. Blood flow measurements dropped by 50–85% from pre-burn levels within 30 minutes of the burn. Flow increased over the 10-day period by 66–200%. Treatment of the burns with the present composition resulted in better blood flow in the burn area at days 2–10 after the burn injury as compared to sulfadiazine. These differences were judged to be statistically significant at days 3, 4, and 8.

Figure 4:
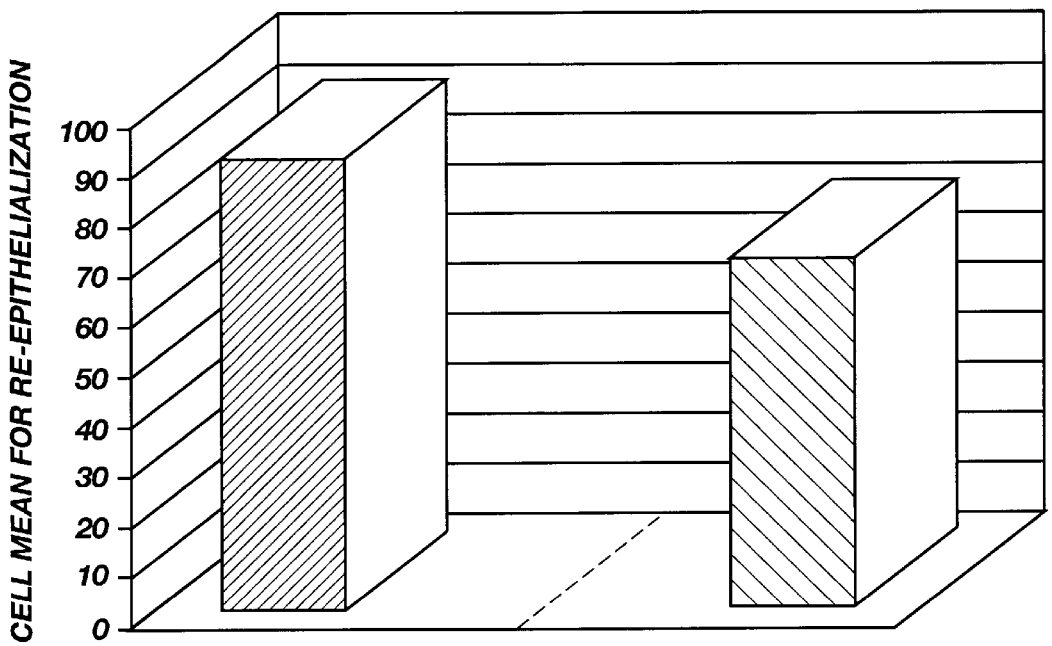
FIG. 4 shows a histogram of the percent of re-epithelialization after burn injury as a function of treatment with either sulfadiazine (light bar) or the present composition (dark bar).

FIG. 4 shows the results of the epithelial response to treatment with the present composition and sulfadiazine. By post-burn day 10, linear re-epithelialization was 91±3% in the wounds treated with the present composition and 70±7% in the wounds treated with sulfadiazine. These results were statistically significant ($p<0.006$).

Figure 5:
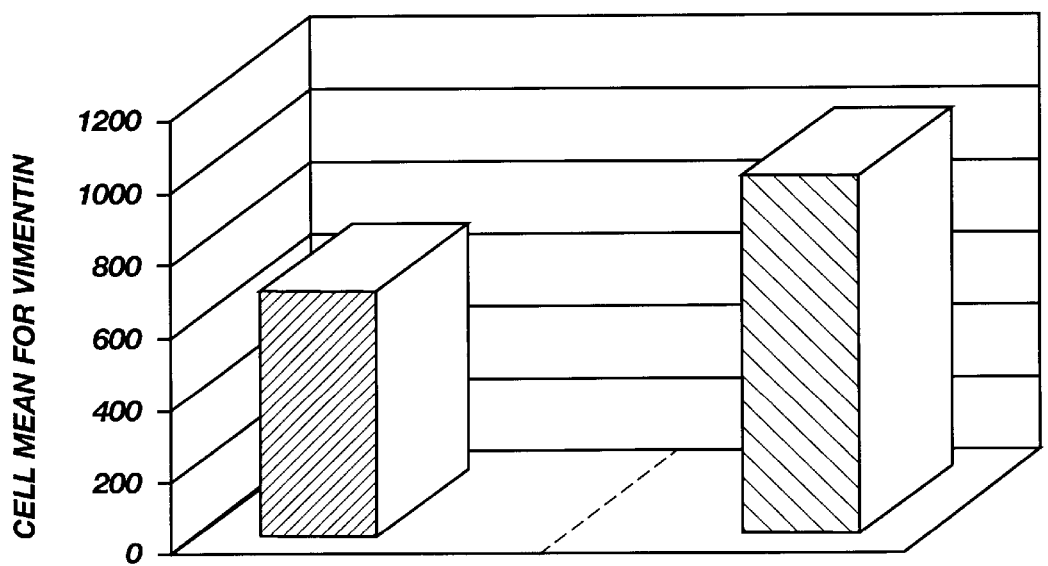
FIG. 5 shows a histogram of cell mean for vimentin test as a function of treatment with sulfadiazine (light bar) or the present composition (dark bar).

FIG. 5 shows the results of the mesenchymal response. On post-burn day 3, vimentin expression was 684±143 mcm in wounds treated with the present composition and 994±114 mcm in the sulfadiazine-treated wounds from the basement membrane.

These results show that partial thickness wounds in this porcine model, which is considered by those skilled in the art as being reasonable predictive of results that would be obtained in humans, maintain equivalent blood flow throughout the time period studied, but show an increase in epithelialization and a trend toward more superfial expression of vimentin in the wounds treated with the present composition. This may represent a difference in the physical environment of these wounds or an effect of sulfadiazine on keratinocyte growth, as has been previously demonstrated in cell culture. The present composition appears to be advantageous to wound epithelialization as compared to sulfadiazine.

I claim:

1. A method of promoting healing and epithelialization of a wound on the skin of a warm-blooded animal comprising applying a composition comprising a stable, water-soluble, biocompatible, thixotropic hydrogel comprising about about 0.01 to 20% by weight of tea tree oil, about 0.0003 to 0.5% by weight of chlorobutanol, about 0.0003 to 0.5% by weight of triclosan, about 0.01 to 1% by weight of polyoxyethylene alkylphenol, about 0.1 to 10% by weight of carboxymethylcellulose, about 0.025 to 0.5% by weight of ethanol, about 0.1 to 1.5% by weight of propylene glycol, an amount of an acid, base, or buffer sufficient to adjust the pH to about 5.5 to 7.0, and the rest water, to the wound for at least about 20 minutes.

2. The method of claim 1 wherein said topical wound treatment composition further comprises about 0.003–0.5% by weight of a preservative selected from the group consisting of methylparaben, propylparaben, methylchloroisothiazolinone, metholisothiazolinone, and diazolidinyl urea.

3. The method of claim 1 wherein said topical wound treatment composition further comprises about 0.01–1% by weight of a surfactant selected from the group consisting of polyoxyethylene alcohols, alkyl ether sulfates, and alkyl sulfates.

4. The method of claim 1 wherein said topical wound treatment composition further comprises about 0.1–10% by weight of a member selected from the group consisting of hydroxypropylcellullose, hydroxyethylcellulose, hydroxymethylcellulose, methylcellulose, polyvinylpyrrolidone, polyvinyl alcohol, and mixtures thereof.

5. A method of making a topical wound treatment composition comprising the steps of:
   (a) dissolving about 0.003 to 0.5 parts by weight of chlorobutanol in about 0.025 to 0.5 parts by weight of ethanol;
   (b) adding about 0.01 to 1 parts by weight of polyoxyethylene alkylphenol to the chlorobutanol and ethanol, followed by adding about 0.003 to 0.5 parts by weight of triclosan and about 0.1 to 10 parts by weight of carboxymethylcellullose;
   (c) then adding about 0.1 to 1.5 parts by weight of propylene glycol and stirring thoroughly;
   (d) next adding a portion of about 78 to 98.9 parts by weight of water and mixing thoroughly to result in a concentrated gen base;
   (e) placing the remaining portion of the water in a separate container and adding the concentrated gel base thereto with agitation until the resulting mixture is smooth;
   (f) mixing about 0.01 to 20 parts by weight of tea tree oil with the smooth mixture; and
   (g) adding an effective amount of an acid base, or buffer to the mixture to obtain a pH of 5.5 to 7.0 and mixing until a smooth thixotropic gel is formed.

6. A composition prepared according to the method of claim 5.

* * * * *